United States Patent
Hendel et al.

(10) Patent No.: US 6,812,348 B1
(45) Date of Patent: Nov. 2, 2004

(54) METHOD FOR PRODUCING 2-CHLORO-5-CHLOROMETHYL-1,3-THIAZOL

(75) Inventors: Wolfram Hendel, Leonding (AT); Sylvia Krich, Altenberg (AT)

(73) Assignee: DSM Fine Chemicals Austria Nfg GmbH & Co KG, Linz (AU)

( * ) Notice: Subject to any disclaimer, the term of this patent is extended or adjusted under 35 U.S.C. 154(b) by 0 days.

(21) Appl. No.: 10/111,011

(22) PCT Filed: Oct. 20, 2000

(86) PCT No.: PCT/EP00/10318

§ 371 (c)(1),
(2), (4) Date: Apr. 19, 2002

(87) PCT Pub. No.: WO01/36400

PCT Pub. Date: May 25, 2001

(30) Foreign Application Priority Data

Nov. 15, 1999 (AT) ............................................. 1914/99
Jan. 14, 2000 (AT) ........................................ A 46/2000

(51) Int. Cl.$^7$ ............................................. C07D 277/20

(52) U.S. Cl. ................................................... 548/202

(58) Field of Search ........................................ 548/202

(56) References Cited

FOREIGN PATENT DOCUMENTS

| EP | 0 446 913 A | 9/1991 |
|----|-------------|--------|
| EP | 0 763 531 A | 3/1997 |
| EP | 0 780 384 A | 6/1997 |
| EP | 0 794 180 A | 9/1997 |

OTHER PUBLICATIONS

Goebel et al., "Synthetic Approaches Towards CGA 293'343: a novel broad–spectrum insecticide", *Pesticide Science*, vol. 55, No. 3, 1999, pp. 355–357.

*Primary Examiner*—Joseph K. McKane
*Assistant Examiner*—Ebenezer Sackey
(74) *Attorney, Agent, or Firm*—Wenderoth, Lind & Ponack L.L.P.

(57) ABSTRACT

The invention relates to a method for producing 2-chloro-5-chloromethyl-1,3-thiazol from compounds of formula (I), wherein X means Cl, —OR, —SR or $NR_2$, R being H or a suitable protective group; Y means H or Cl and Z means Cl or O, the compounds of formula (I) having at most one double bond between C* and C" or between C" and Z, on the condition that the bond between C" and Z is a double bond when Z is the same as O and a single bond when Z is the same as Cl; with the following intermediate stage: $A_1$) reacting 2,3-dichloropropanal with rhodanide and acetalising to 3-chloro-1,1-dialkoxy-2-isothiocyanato-propane or $a_2$) reacting 2,3-dichloropropanal with thiourea to form a mixture of the hydrochlorides of the compounds N-[[5-(2-aminothiazol)yl]methyl]thiourea and [5-(2-aminothiazol)yl]methylthioformamidine and splitting to obtain the corresponding thiol or amine or b) reacting a compound of formula (I) wherein X means OR, SR or $NR_2$, Y means clorine and Z means oxygen with thiourea to produce the compound of formula (V), or c) reacting a compound of formula (I), wherein X means OR, SR or $NR_2$, Y means chlorine and Z means oxygen with ammoniumdithiocarbamate or ammoniumthiocarbamate, to produce the compound (VIa) or (VIb); d) converting 1,2,3-trichloropropane to the corresponding thiazolidine and then dehydrogenating or e) converting 1,3-dichloro-prop-1-ene to the corresponding epoxide and then reacting said epoxide with thiourea ($e_1$) or ammoniumdithiocarbamate or ammoniumthiocarbamate ($e_2$).

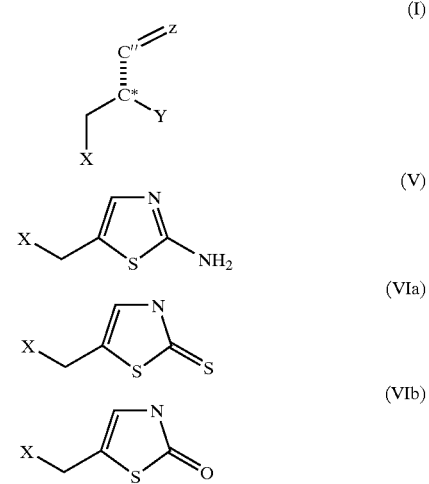

3 Claims, No Drawings

METHOD FOR PRODUCING 2-CHLORO-5-CHLOROMETHYL-1,3-THIAZOL

The invention relates to a process for the preparation of 2-chloro-5-chloromethyl-1,3-thiazole (CCT), and also intermediates used therein.

2-Chloro-5-chloromethyl-1,3-thiazole is a useful intermediate in the preparation of pesticides or of pharmaceutical products.

The literature discloses a multiplicity of highly varied processes for the preparation of CCT. For example, EP 0 260 560 and EP 0 446 913 describe the preparation of CCT by reaction of allyl isothiocyanate or an allyl isothiocyanate substituted with a leaving group with a chlorinating agent, and EP 0 763 531 describes the reaction of 2-chloroallyl isothiocyanate with a chlorinating agent. These processes have disadvantages in that, for example, several by-products occur in the first variant, which cause CCT prepared in this way to have a low purity, and the starting material in the second variant can only be obtained at high cost. Further, a considerable excess of chlorinating agents must be used and the process must be operated at high dilution. Also, exact control of the reaction temperature is necessary and the stable intermediates formed in the course of the reaction have to be converted exothermically to the desired final product in an additional reaction step. EP 0 794 180 describes the preparation of CCT from 1,3-dichloropropene and a thiocyanate salt via 3-chloro-1-isothiocyanate-1-propene as an improvement.

Other variants, such as the process according to EP 0 775 700, in which the CCT is prepared via 2-amino-5-methylthiazole by means of diazotization and subsequent chlorination, also have the disadvantage that CCT is contaminated by a multiplicity of by-products, which are very difficult or impossible to remove and lead to high yield losses.

It is an object of the invention to provide novel processes which facilitate the preparation of the CCT in high purity and yield.

The invention accordingly provides a process for the preparation of 2-chloro-5-chloromethyl-1,3-thiazole, which comprises reacting a compound of the formula

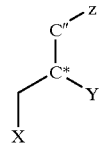

(I)

in which X is Cl, —OR, —SR or —NR$_2$, where R is H or a suitable protecting group; Y is H or Cl; and Z is Cl or O, the compounds of the formula (I) having a maximum of one double bond between C* and C" or between C" and Z, with the proviso that the bond between C" and Z is a double bond when Z is O and is a single bond when Z is Cl, a) where X and Y are Cl and Z is O either a$_1$) first with thiocyanate to give a compound of the formula

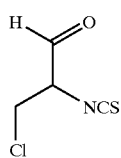

(II)

and then with an acid/R'OH or acid/orthoester mixture, where R' is C$_1$ to C$_6$-alkyl, to give the compound of the formula

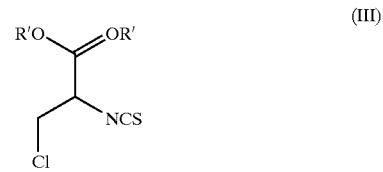

(III)

or first converting the compound of the formula (I) to the acetal and then reacting with thiocyanate to give the compound of the formula (III), then converting it to 2-chloro-5-chloromethyl-1,3-thiazole, or a$_2$) with thiourea to give; a mixture of compounds of the formulae

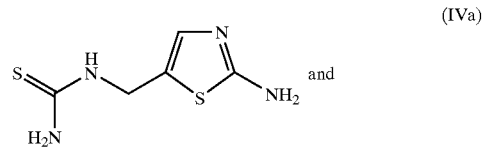

(IVa)

(IVb)

and, after basic cleavage to give the corresponding thiol or amine, converting to 2-chloro-5-chloromethyl-1,3-thiazole by Sandmeyer diazotization and optional reaction with a chlorinating agent or b) where X is OR, SR or NR$_2$, and R is H or a suitable protecting group, Y is Cl and Z is O, with thiourea to give a compound of the formula

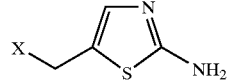

(V)

and then substituting the amino group by a chlorine atom by Sandmeyer reaction, and obtaining 2-chloro-5-chloromethyl-1,3-thiazole by chlorination and optional ether cleavage or c) where X is OR, SR or NR$_2$, and R is H or a suitable protecting group, Y is Cl and Z is O, with ammonium dithiocarbamate or ammonium thiocarbamate to give the compound

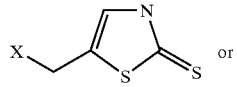

(VIa)

or

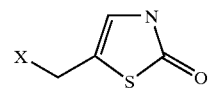

(VIb)

and, if necessary, converting the radical X into the corresponding radical OH, SH or NH$_2$ by removal of the protecting group, and then obtaining 2-chloro-5-chloromethyl-1,3-thiazole by reaction with suitable chlorinating agents, or d) where X, Y and Z are all Cl, and the compound contains no double bonds,
with thiourea to give a thiazolidine of the formula

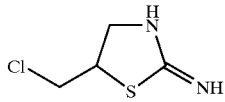
(VII)

and then dehydrogenating and diazotizing to give 2-chloro-5-chloromethyl-1,3-thiazole or e) where X and Z are both Cl and Y is H, and the compound contains a double bond between C* and C", with an oxidizing agent to convert it to the corresponding epoxide, which e$_1$) is converted directly to 2-amino-5-chloromethyl-1,3-thiazole using thiourea in a suitable solvent and/or is converted to the compound of the formula (V), where X is OR', and R' is H or C$_1$–C$_6$-alkyl, and is then converted to 2-chloro-5-chloromethyl-1,3-thiazole by diazotization and, if necessary, ether cleavage and/or chlorination, or e$_2$) similarly to c), is converted to 2-chloro-5-chloromethyl-1,3-thiazole by reaction with ammonium dithiocarbamate or ammonium thiocarbamate.

According to the invention, CCT is prepared by starting from a compound of the formula (I) in which X is Cl, —OR, —SR or —NR$_2$, where R is H or a protecting group; Y is H or Cl and Z is Cl or O, the compounds of the formula (I) having a maximum of one double bond between C* and C" or between C" and Z, with the proviso that the bond between C" and Z is a double bond when Z is O and is a single bond when Z is Cl.

In the formula (I), the radical R is H or a protecting group. Useful protecting groups include all groups suitable for protection of the oxygen, sulfur or nitrogen radical. These include C$_1$–C$_6$-alkyl groups, such as methyl, ethyl, propyl, i-butyl, t-butyl, hexyl, or the phthalimide group.

Variant a):

In variant a), X and Y are both chlorine and Z is oxygen, so that 2,3-dichloropropanal is used as starting compound of the formula (I).

2,3-Dichloropropanal is easily accessible, for example by chlorination of acrolein in dichloromethane. According to the invention, the conversion of the aldehyde to CCT can be carried out by the variants a$_1$) or a$_2$).

Variant a$_1$):

Variant a$_1$) involves aldehyde first being reacted with sodium or ammonium thiocyanate to give the compound of the formula (II). The thiocyanate can be used in an equimolar quantity, or in excess or deficiency based on the aldehyde. Thiocyanate is preferably used in deficiency. The reaction takes place in a suitable solvent. Suitable solvents include all customary organic solvents, for example carboxylic acids having from 1 to 6 carbon atoms, such as formic acid, acetic acid, propionic acid, etc.; halogenated aliphatic and aromatic hydrocarbons, such as methylene chloride, trichloromethane, trichloroethylene, carbon tetrachloride, chlorobenzene, dichlorobenzene etc.; alcohols, such as methanol, ethanol, propanol, t-butanol, etc.; ethers, such as diethyl ether, dipropyl ether, diisopropyl ether, dibutyl ether, t-butyl methyl ether, ethylene glycol monomethyl ether, tetrahydrofuran, dioxane etc; ketones, such as acetone, methyl ethyl ketone, methyl i-butyl ketone, cyclohexanone etc.; amides, such as N,N-dimethylformamide, N,N-diethylformamide, N-methylpyrrolidone, etc.; sulfoxides, such as dimethyl sulfoxide, etc. and nitriles, such as acetonitrile, propionitrile, etc.

Further useful solvents include water or solvent/water mixtures.

It can also be advantageous to add a phase transfer catalyst to the solvent. The preferred quantity of added phase transfer catalyst is in the range from 0.1 to 15 mol %. Useful phase transfer catalysts include crown ethers, quaternary ammonium salts, such as tetramethylammonium chloride, tetraethylammonium chloride, tetrabutylammonium chloride, benzyltrimethylammonium chloride, and also quaternary phosphonium salts.

Preferred solvents in the variant a$_1$) are C$_1$–C$_3$-carboxylic acids, nitriles, chlorinated aliphatic hydrocarbons and amides. Most preferred are acetic acid, acetonitrile, dimethylformamide and a methylene chloride/crown ether mixture.

The temperature is in the range from 10 to 150° C., more preferably from 15 to 130° C., most preferably from 20 to 80° C.

The compound of the formula (II) is novel and therefore likewise forms part of the subject matter of the invention.

The compound of the formula (II) is then converted to the acetal of the formula (III) by addition of an acid/R'OH or acid/orthoester mixture at from 10 to 100° C.

Useful acids include HCl and p-toluenesulfonic acid. Useful alcohols R'OH include C$_1$–C$_6$-alcohols, such as methanol or ethanol and propanol. Preference is given to ethanol.

Useful orthoesters include alkyl orthoformates, such as methyl orthoformate or ethyl orthoformate.

The compound of the formula (III) is novel and therefore likewise forms part of the subject matter of the invention.

However, the aldehyde can also first be converted to the corresponding acetal. This conversion is carried out in a similar fashion to the above process. The acetal is then converted to the compound of the formula (III) by reaction with sodium or ammonium thiocyanate, again in a similar fashion to the above process.

The compound of the formula (III) is then converted to 2-chloro-5-chloromethyl-1,3-thiazole by suitable steps, such as rearrangements, alcohol elimination, or ether cleavage, reaction with a chlorinating agent etc.

It is further possible to convert the aldehyde of the formula (II) directly to 2-chloro-5-chloromethyl-1,3-thiazole by means of suitable steps.

Variant a$_2$):

Variant a$_2$) first involves reaction of the aldehyde of the formula (I) with thiourea to give a mixture of the compounds N-[[5-(2-aminothiazol)yl]-methyl]thiourea and [5-(2-aminothiazol)yl]methylthioformamidine of the formulae (IVa) and (IVb), which occur in the form of their hydrochloride salts. From 0.8 to 2 equivalents of thiourea are preferably used. The reaction takes place in one of the solvents listed under variant a$_1$). Preference is given to ketones, such as methyl i-butyl ketone or acetone, or alcohols, such as methanol, ethanol or butanol.

The reaction temperature is in the range from 15° C. and the boiling point of the solvent used.

The compounds of the formulae (IVa) and (IVb), and their hydrochloride salts are also novel and therefore likewise form part of the subject matter of the invention.

The conversion to CCT takes place by basic cleavage in the corresponding thiol or amine, subsequent Sandmeyer diazotization and, if necessary, chlorination.

The Sandmeyer diazotization takes place under the reaction conditions customary for this type of reaction, for example using inorganic or organic nitrites, preferably using sodium nitrite or t-butyl nitrite in HCl (e.g. aqueous HCl) or mixtures of HCl and an organic polar solvent, such as acetonitrile, in the optional presence of a copper halide catalyst.

Useful chlorinating agents include those compounds that have reactive chloride atoms under the reaction conditions. These are, for example, $Cl_2$, sulfuryl chloride, $PCl_5$, $PCl_3$, $POCl_3$ etc.

The operation of the chlorination reaction generally takes place by the usual methods.

Variant b):

In variant b), X is a radical —OR, —SR or —$NR_2$ where R is H or suitable protecting group; Y is Cl and Z is oxygen.

The corresponding aldehyde is reacted with thiourea to give the compound of the formula (V). Thiourea is used in an equimolar quantity, or in excess or deficiency. Thiourea is preferably used in a small deficiency based on the aldehyde. The amino group is then exchanged for a chlorine atom by a Sandmeyer reaction in a similar fashion to variant $a_2$)

In order to obtain CCT, the ether group is then optionally cleaved and the corresponding radical substituted by a chlorine atom. The cleavage and chlorination are likewise carried out in a similar fashion to $a_2$).

Variant c):

In variant c), X is OR, SR or $NR_2$ where. R is H or suitable protecting group, Y is Cl and Z is O.

The corresponding compound of the formula (I) is either reacted with ammonium dithiocarbamate or with ammonium thiocarbamate to give the compound of the formula (VIa) or (VIb) respectively.

Useful solvents again include those listed under variant $a_1$). Preference is given to amides, alcohols or nitriles. The reaction is more preferably carried out in DMF, methanol or ethanol, or acetonitrile.

The reaction temperature is in the range from 0° C. to the boiling point of the solvent used.

If necessary, the radical X is cleaved by known methods for protecting group cleavage, which gives the corresponding radical OH, SH or $NH_2$. Depending on the protecting group, the cleavage takes place, for example, under acidic, basic or hydrogenolytic conditions.

The further conversion to give CCT takes place by reaction with suitable chlorinating agents in a similar fashion to variant $a_2$).

Variant d)

In variant d), X, Y and Z are all chlorine atoms and the compound has no double bond. The starting compound is therefore 1,2,3-trichloropropane, which is reacted with thiourea to give the thiazolidine of the formula (VII). Again, thiourea can be used in an equimolar quantity, or in a less or greater than stoichiometric quantity based on trichloropropane. Useful solvents are those listed under variant $a_1$). The reaction temperatures are in the range from 0° C. to the boiling point of the solvent used.

Thiazolidine is then dehydrogenated by addition of customary oxidizing agents for aromatization (customary dehydrating agents), such as sulfur, chloranil, DDQ, platinum oxide etc., under the customary conditions for dehydrogenations.

Finally, the Sandmeyer diazotization to give CCT is carried out in a similar fashion to variant $a_2$) under the customary reaction conditions for diazotization reactions.

Variant e):

In variant e), X and Z are chlorine atoms, Y is H and the compound has a double bond between C* and C''. The starting compound is therefore 1,3-dichloro-1-propene, which is converted to 2-chloro-3-chloromethyl-oxirane under conditions disclosed in the literature by a suitable oxidizing agent, such as a peroxy acid, an acid/$H_2O_2$ mixture, inorganic or organic peroxides, or hydroperoxides.

Useful solvents include nitriles, such as acetonitrile, or chlorinated hydrocarbons, such as chloroform, carbon tetrachloride, methylene chloride, 1,2-dichloroethane or chlorobenzene.

Useful peroxy acids include, for example, peracetic acid, m-chloroperbenzoic acid etc.

According to variant $e_1$), the oxirane or epoxide obtained is then converted to the compound of the formula (V) by thiourea in a suitable solvent in a similar fashion to the other variants. Useful solvents are those listed under variant $a_1$). Useful solvents of the variant $e_1$) are alcohols, in particular methanol, ethanol and t-butanol, ketones, in particular acetone, nitriles, in particular acetonitrile, ethers, in particular tetrahydrofuran, dimethoxyethane, amides, in particular N-methylpyrrolidone, water or mixtures of water, in particular acetone/$H_2O$ or acetonitrile/$H_2O$ mixtures. Mixtures of an alcohol with other solvents, for example with dichloromethane, can also be used. Solvent mixtures with an alcohol, in particular methanol, and dichloromethane are therefore also preferred. When a solvent mixture is used, it can be advantageous to additionally add a suitable base, such as a trialkylamine.

Depending on the choice of solvent, 2-amino-5-chloromethyl-1,3-thiazole is formed directly or the compound of the formula (V) with identical R and R' is first formed or also mixtures of 2-amino-5-chloromethyl-1,3-thiazole and 2-amino-5-alkoxymethyl-1,3-thiazole and/or 2-amino-5-hydroxymethyl-1,3-thiazole. The compound of the formula (V) where X is OR' is formed in particular when an alcohol is used as solvent.

The compound obtained by the reaction with thiourea or the mixture of the above compounds is then converted to CCT by diazotization and, if necessary, ether cleavage and/or chlorination. The sequence of these steps may vary.

Similar to the other variants, the exchange of the amino group for a chlorine atom takes place by diazotization.

If the compound of the formula (V) where X is OR' or a mixture as described above is obtained in the first step, the ether group, if necessary, must be cleaved and a chlorination carried out in a similar fashion to the previously described variants, in order to obtain CCT. The ether cleavage., and also the chlorination, can take place before, after the diazotization or sometimes also simultaneously with the diazotization.

It is also possible to carry out the ether cleavage and the chlorination in a single step. The $C_1$–$C_6$-alkoxyl group of the radical OR' is preferably replaced directly, i.e. in a single step, by Cl, by reaction with $POCl_3$ or with acetyl chloride, optionally in combination with a Lewis acid, such as $ZnCl_2$, $AlCl_3$ or $BCl_3$, or with dry HCl in combination with a Lewis acid, such as $ZnCl_2$, $AlCl_3$ or $BCl_3$.

A further alternative to the previously described chlorination steps to replace the $C_1$–$C_6$-alkoxyl group or the hydroxyl group of the radical OR' by a chlorine atom is the reaction of the corresponding thiazole with thionyl chloride.

In variant $e_2$), oxirane or epoxide obtained is reacted with ammonium dithiocarbamate or ammonium thiocarbamate to give CCT in a similar fashion to variant c), which makes any cleavage of the radical X required in variant $e_1$) unnecessary.

The isolation and workup of the CCT prepared takes place, depending on the chosen preparation variant, by customary methods, such as extraction, distillation, etc.

EXAMPLE 1

Preparation of N-[[5-(2-aminothiazol)yl]-methyl] thiourea and [5-(2-aminothiazol)yl]-methylthioformamidine 4.8 g (37.8 mmol) of 2,3-dichloropropionaldehyde were heated with 2.80 g (36.8 mmol) of thiourea in 25 ml of absolute ethanol for 3 hours to boiling. The resulting solid was filtered off, and then digested with hot ethanol and twice with acetone.

Yield: 2.05 g (42% of the theory)

Analyses:

$^1$H-NMR (DMSO-$d_6$): δ (ppm): 9.70 (s; 1H; broad); 9.63 (s; 2H, broad); 9.43 (s; 2H, broad); 7.43 (s; 1H); 4.81 (s; 2H).

$^{13}$C-NMR (DMSO-$d_6$): δ (ppm): 170.7 (s); 169.3 (s); 125.3 (d); 120.1 (s); 28.6 (t).

Elemental analysis: calculated: C: 22.99%; H: 3.86; N: 21.54; Cl 27.15%; S: 24.55% Found: C.22.9%; H: 3.9%; N: 21.4%; Cl: 27.1%; S: 24.5%.

EXAMPLE 2

3-Chloro-2-isothiocyanatopropanal

Method A 36.35 g (0.29 mol) of 2,3-dichloropropionaldehyde and 23.51 g (0.29 mol) of sodium thiocyanate were heated in 250 ml of glacial acetic acid for 2 hours at 50° C. The solvent was stripped off, the residue taken up in 500 ml of methylene chloride and the resulting precipitate filtered off. The filtrate was washed twice with 200 ml of water each time, dried over sodium sulfate and the solvent stripped off.

Yield: 32.10 g of 3-chloro-2-isothiocyanatopropanal; orange-yellow oil (74% of the theory).

Method B 6.35 g (50 mmol) of 2,3-dichloropropionaldehyde and 2.43 g (30 mmol) of sodium thiocyanate were heated in 15 ml of acetonitrile for 3 hours to boiling. The suspension was filtered and the filtrate freed of solvent. The residue was dissolved in 50 ml of methylene chloride, the insoluble portion was filtered off, the filtrate was washed twice with 10 ml of water each time and the product solution dried by azeotropic distillation.

Yield: corresponds to the theoretical yield according to GC.

Analyses:

Kp: 60–62° C./1 mbar.

$^1$H-NMR (CDCl$_3$): 9.58 (s; 1H); 4.56 (t; 1H; J=5.5 Hz); 4.11 (d; 2H; J=5.5 Hz).

$^{13}$C-NMR (CDCl$_3$): 192.9 (d); 134.3 (s, very small); 60.3 (d); 47.5 (t).

EXAMPLE 3

3-chloro-1,1-diethoxy-2-isothiocyanato-propane 6.75 g (45 mmol) of 3-chloro-2-isothiocyanatopropionaldehyde were dissolved in 67 ml of ethanol, 67 ml of concentrated hydrochloric acid were added and the mixture heated for 2 hours to boiling. The reaction solution was extracted 4 times with 100 ml of methylene chloride in each case, the united organic phases washed with water and sodium hydrogencarbonate solution and then the solvent stripped off, which gave 3-chloro-1,1-diethoxy-2-isothiocyanatopropane.

Analyses:

$^1$H-NMR (CDCl$_3$): δ (ppm): 4.59 (d; 1H; J=5.2 Hz); 4.01–3.92 (m; 1H); 3.91 (t; 2H; J=5.7 Hz); 3.82–3.70 (m, 2H); 3.68–3.56 (m; 2H); 1.29–1.18 (m; 6H).

$^{13}$C-NMR (CDCl$_3$): δ (ppm): 102.6 (d); 66.9 (t); 64.3 (t); 59.8 (d); 48.0 (t); 15.5 (q).

GC/MS: m/z: 103, 47, 75, 29, 72, 27, 150, 178, 59, 142, 152, 180.

EXAMPLE 4

2-Chloro-5-methoxymethylthiazole

A solution of 1.29 g (17 mmol) of thiourea in 15 ml of methanol was added dropwise to 2.54 g (20.0 mmol) of 1,3-dichloropropene oxide in 6 ml of methanol and then first stirred for an hour at room temperature and then for a further hour at the boiling temperature.

The solvent was stripped off, the residue partitioned between sodium hydrogencarbonate solution and tert-butyl methyl ether and the intermediate exhaustively extracted.

The intermediate (1.40 g) was dissolved in 5 ml of hydrochloric acid and 1.6 ml of acetonitrile, and mixed at 2° C. with 0.9 g (9.4 mmol) of copper(I) chloride, then a solution of 1.51 g (13.2 mmol) of tert-butyl nitrite in 1.6 ml of acetonitrile was slowly added dropwise at from −8° C. to 0° C. Stirring was then continued for 2 hours at from 0 to 5° C. and for a further hour at room temperature.

The reaction mixture was filtered and then exhaustively extracted with chloroform. The organic phases were washed with sodium hydrogencarbonate solution and water and freed of solvent.

Yield: 1.31 g of 2-chloro-5-methoxymethylthiazole; yellow oil (40% of the theory).

Analyses:

$^1$H-NMR (CDCl$_3$): δ (ppm): 7.41 (s; 1H); 4.56 (s; 2H); 3.40 (s; 3H).

GC-MS: m/z: 163, 128, 72, 57.

EXAMPLE 5

Further Processing of 2-chloro-5-methoxy-methylthiazole to Give CCT

Method A)

0.1 g (0.61 mmol) of 2-chloro-5-methoxymethylthiazole, prepared according to Example 4, was stirred in a mixture of 1 ml of water, 1 ml of sulfuric acid and 0.5 ml of hydrochloric acid for 5 hours at room temperature and for a further 5 hours at 50° C. The reaction solution was extracted with toluene and the extract analyzed by means of GC-MS. CCT could be unambiguously identified as the final product with the aid of comparative spectra.

GC/MS: m/z: 128, 132, 45, 163, 134, 71, 29, 72, 57, 58, 39, 79, 165.

Method B)

2.00 g (12.22 mmol) of 2-chloro-5-methoxymethylthiazole, prepared according to Example 4, were heated with 4.00 g (26.20 mmol) of phosphorus oxychloride for 12 hours at 80° C. The reaction mixture was then poured into ice-water and extracted 3 times with methylene chloride. The extract contained CCT as the main product, which could be unambiguously identified with the aid of comparative spectra. By-products were not observed by GC.

EXAMPLE 6

2-Chloro-5-methoxymethylthiazole

A solution of 3.65 g (48 mmol) of thiourea in 50 ml of methanol was added dropwise to 7.62 g (60.0 mmol) of 1,3-dichloropropene oxide in 18 ml of methanol at 2° C. and then stirred for an hour at the boiling temperature.

The solvent was stripped off, the intermediate (10.1 g) dissolved in 25 ml of hydrochloric acid and 8 ml of acetonitrile and mixed with 4.75 g (48 mmol) of copper(I) chloride at 2° C., then a solution of 6.93 g (67.2 mmol) of tert-butyl nitrile in 8.2 ml of acetonitrile was slowly added dropwise at from −10° C. to −5° C. The mixture was then stirred for a further 3 hours at room temperature.

The reaction mixture was filtered and then exhaustively extracted by chloroform. The organic phases were washed with sodium hydrogencarbonate solution and water and freed of solvent.

Yield: 7.05 g of 2-chloro-5-methoxymethylthiazole; yellow oil (90% of the theory).

Analyses:

$^1$H-NMR (CDCl$_3$): δ (ppm): 7.41 (s; 1H); 4.56 (s; 2H); 3.40 (s; 3H).

GC-MS: m/z: 163, 128, 72, 57.

EXAMPLE 7

Further Processing of 2-chloro-5-methoxymethylthiazole to CCT 0.1 g (0.61 mmol) of 2-chloro-5-methoxymethylthiazole, prepared according to Example 6, were stirred in a mixture of 1 ml of water, 1 ml of sulfuric acid and 0.5 ml of hydrochloric acid for 5 hours at room temperature and for a further 5 hours at 50° C. The reaction solution was extracted with toluene and the extract analyzed by means of GC-MS. CCT could be unambiguously identified as the final product with the help of comparative spectra.

EXAMPLE 8

98.8 g (0.89 mol) of. 1,3-dichloropropene were dissolved in 400 g of 1,2-dichloroethane and mixed with 155.6 g (0.9 mol) of dried 3-chloroperbenzoic acid and heated for 40 hours at 60° C. The reaction mixture was cooled to −5° C., 3-chlorobenzoic acid filtered off and the filtrate washed with saturated sodium hydrogencarbonate solution and 10% sodium pyrosulfite solution. The aqueous phases were extracted once with chloroform and then the united organic phases were dried over sodium sulfate, filtered and the solvent stripped off. Finally, the product is distilled at 80–83° C./60 mbar.

Yield: 84.75 g of 1,3-dichloropropene oxide; colorless liquid (83% of the theory; 88% pure).

1.29 g (17.0 mmol) of thiourea and 2.54 g (17.0 mmol) of 88% 1,3-dichloropropene oxide in 21 ml of 1,2-dimethoxyethane were heated for 2 hours at 60° C. and the solvent was stripped off.

The crude 2-amino-5-chloromethylthiazole was suspended in 10 ml of concentrated hydrochloric acid and 3.4 ml of acetonitrile and mixed at from −13 to −7° C. first with 1.98 g (20 mmol) of copper(I) chloride, then slowly with 2.89 g (28 mmol) of tert-butyl nitrile in 3.4 ml of acetonitrile and stirred for 2 hours at room temperature.

The reaction solution was diluted with 20 ml of water, exhaustively extracted by dichloromethane and finally the solvent was stripped off. This crude product, which as well as 37% by weight of CCT also contained 2-chlorohydroxymethylthiazole, was mixed with 1 ml of thionyl chloride and stirred for an hour at room temperature. The reaction solution was hydrolyzed with 25 g of ice, exhaustively extracted with dichloromethane and finally the solvent was stripped off.

Yield: 2.42 g of CCT; brown oil (purity 52% by weight; 44% of the theory).

We claim:

1. A process for the preparation of 2-chloro-5-chloromethyl-1,3-thiazole, which comprises reacting 1,3-dichloro-1-propene with an oxidizing agent selected from peroxy acids, an acid/H$_2$O$_2$ mixture, inorganic or organic peroxides or hydroperoxides in a solvent selected from nitriles or chlorinated hydrocarbons to convert it to the corresponding epoxide, which is a$_1$) converted directly to 2-amino-5-chloromethyl-1,3-thiazole by thiourea in a suitable solvent selected from C$_1$–C$_6$-carboxylic acids, halogenated aliphatic or aromatic hydrocarbons, ethers, ketones, amides, sulfoxides or nitriles and is then converted to 2-chloro-5-chloromethyl-1,3-thiazole by Sandmeyer diazotization in the presence of inorganic or organic nitrites in HCl or in mixtures of HCl and an organic polar solvent, optionally in the presence of a copper halide catalyst or a$_2$) is first converted to the compound of the formula (I)

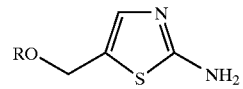

wherein R is C$_1$–C$_6$ alkyl, by thiourea in the presence of an alcohol ROH, wherein R is C$_1$–C$_6$ alkyl, optionally in combination with a solvent selected from the group of C$_1$–C$_6$-carboxylic acids, halogenated aliphatic or aromatic hydrocarbons, ethers, ketones, amides, sulfoxides or nitriles and is then converted to a compound of the formula (II)

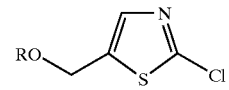

wherein R is C$_1$–C$_6$ alkyl, by Sandmeyer diazotization, whereupon 2-chloro-5-chloromethyl-1,3-thiazole is obtained after ether cleavage and chlorination.

2. The process as claimed in claim 1, wherein, in variant a$_2$, the ether cleavage and chlorination take place in a single step which involves substituting the C$_1$–C$_6$ alkoxyl group of the compounds of the formula II directly by a chlorine atom by reaction with POCl, or an acetyl chloride, optionally in combination with a Lewis acid, or with dry HCl in combination with a Lewis acid.

3. The process as claimed in claim 1, wherein, in variant a$_2$, the C$_1$–C$_6$-alkoxyl group of the compounds of the formula II is substituted by chlorine by reaction with thionyl chloride.

* * * * *